United States Patent [19]

Bredeson et al.

[11] 4,012,457
[45] Mar. 15, 1977

[54] THERMAL CRACKING METHOD FOR THE PRODUCTION OF ETHYLENE AND PROPYLENE IN A MOLTEN METAL BATH

[75] Inventors: Larry D. Bredeson; Glenn R. McCullough, both of Houston; Oran L. Wylie, Dallas, all of Tex.

[73] Assignee: Shell Development Company, Houston, Tex.

[22] Filed: Oct. 6, 1975

[21] Appl. No.: 619,765

[52] U.S. Cl. .......................... 260/683 R; 208/125; 260/683 RF
[51] Int. Cl.² ...................... C07C 3/00; C07C 5/00; C07C 11/02
[58] Field of Search ................. 260/683 R, 683 RF; 208/125

[56] References Cited

UNITED STATES PATENTS

| | | | |
|---|---|---|---|
| 2,269,485 | 1/1942 | Salmi | 208/125 |
| 2,543,743 | 2/1951 | Evans | 208/125 |
| 3,081,256 | 3/1963 | Hendal et al. | 260/683 R |
| 3,696,166 | 10/1972 | Ozawa et al. | 260/683 R |
| 3,718,708 | 2/1973 | Ozawa et al. | 260/683 R |
| 3,843,744 | 10/1974 | Kramer et al. | 260/683 R |
| 3,876,527 | 4/1975 | Dugan et al. | 260/683 R |

FOREIGN PATENTS OR APPLICATIONS 7,107,881  12/1971  Netherlands ..................... 208/125

OTHER PUBLICATIONS

Chem. Engr. Prog., vol. 53, No. 9, *Comm. Ethylene Prod. by Propane Pyrolysis in a Molten Lead Bath*, Fair et al., Sept., 1957.

*Primary Examiner*—O. R. Vertiz
*Assistant Examiner*—Eugene T. Wheelock
*Attorney, Agent, or Firm*—Dean F. Vance

[57] ABSTRACT

The pyrolysis of hydrocarbons to produce light olefins is accomplished in a reactor-quench system employing a common molten metal medium and forced circulation risers in both the reactor and quench zones.

7 Claims, 1 Drawing Figure

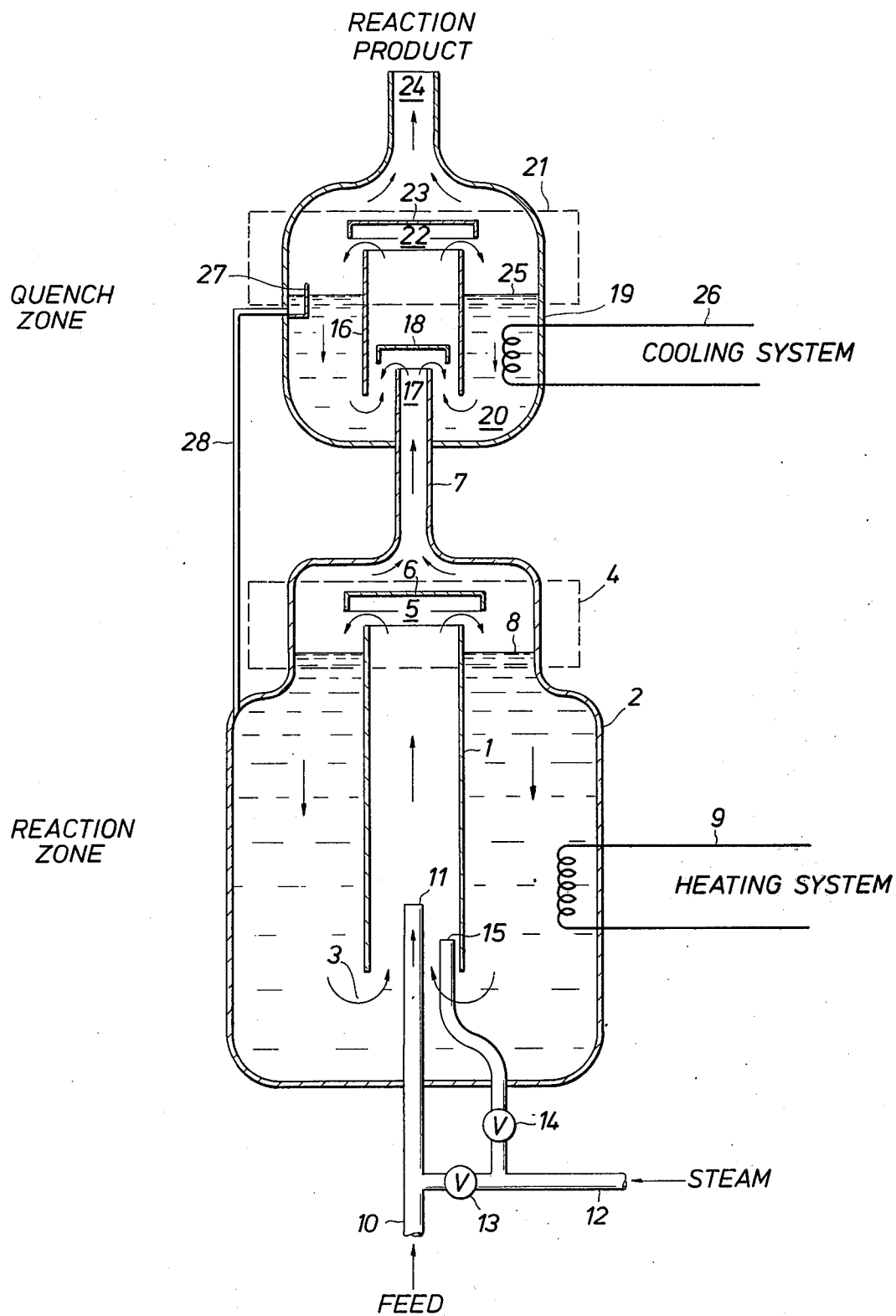

THERMAL CRACKING METHOD FOR THE PRODUCTION OF ETHYLENE AND PROPYLENE IN A MOLTEN METAL BATH

BACKGROUND OF THE INVENTION

1. The Prior Art

The most widely employed method for producing olefins is by the thermal cracking of hydrocarbons in tubular pyrolysis furnaces. However, as economic factors dictate that progressively heavier feedstocks be used for olefin or ethylene manufacture, two shortcomings in the conventional tubular pyrolysis furnace become more apparent. For one, coking rates both in the furnace tubes and in the furnace effluent quench area are greatly increased. In addition, substantial yields of light saturates and heavy cracked liquid by-products increase the capital cost of the downstream product handling facilities and decrease the total value of the yield spectrum.

An alternative approach to the use of tubular pyrolysis furnaces is use of molten bath heat carrier circulation systems. These molten bath heat carrier circulation systems typically are high temperature, low residence time systems which result in certain yield advantages and are of a relatively non-coking nature. See generally Fair et al., Commercial Ethylene Production by Propane Pyrolysis in a Molten Lead Bath, Chemical Engineering Process, Vol. 53, No. 9, pp 433-438 (1957). However, the presently available molten bath cracking systems are far from ideal.

The molten bath cracking system disclosed in Bruns, U.S. Pat. No. 2,931,843, comprises a reactor having a molten lead reservoir wherein the hydrocarbon feed is passed through the reservoir and the resulting cracked gases are quenched by cooled molten lead sprayed from the upper portion of the reactor. There are a number of disadvantages to the Bruns process and apparatus. In Bruns, the molten lead reservoir is relatively static while the hydrocarbon feed is bubbled through the bed. This type of operation at the required high superficial gas velocities leads to severe vibration, slugging and backmixing plus entrainment. The backmixing of reactants results in excessive coke make. Likewise, molten bed reactors employing similar "dip-tube" arrangements have identical problems. Still another serious problem in Bruns arises due to the erosion of the spray-type nozzles employed for quenching.

Another type of molten metal cracking apparatus is disclosed in Ozawa et al., U.S. Pat. No. 3,718,708, where solid grains or oils of high boiling point are employed for contacting purposes in the tubular quench section. This system has obvious disadvantages due to the complexity of the quench system.

Other types of molten medium cracking processes employ molten salts as the heat transfer medium. A representative molten salt process is disclosed in Hendal et al., U.S. Pat. No. 3,081,256. in Hendal et al., the molten salt is circulated by gas-lift action in a riser and is reheated by submerged combustion in a separate section of the reactor vessel. Cracked gases are separated from the molten salt at the top of the riser by a semi-centrifugal separator while coke formed in the reaction is burned off in the submerged regeneration section of the reactor vessel. Quenching of the cracked gas is accomplished by conventional means (steam contacting or heat exchange) downstream of the riser outlet salt separator. While the high heat transfer rates attained in the molten salt riser employed in Hendal et al. allowed shorter residence times and reaction temperatures than conventional tubular pyrolysis furnaces, the process as disclosed has two basic disadvantages. First, since salt is employed as the molten medium, steam or water are typically not employed in the reactor since steam reacts with the salt. Secondly, since the molten salt is not employed as the quench material, it is necessary to prevent molten salt loss from the reaction zone. This requires longer residence time in the separation chamber, therein permitting excessive coke formation and secondary reactions (resulting in the loss of valuable product) prior to quenching of the reaction products.

2. Summary of the Invention

A new process and apparatus for the thermal cracking of gaseous and liquid hydrocarbons is disclosed which improves the yield structure of the gaseous reaction products, reduces coke make, eliminates the problems associated with molten medium carryover in the reaction chamber, and permits the use of steam in the reaction chamber to lower partial pressure thus lowering coke made and improving selectivity to olefin.

In broad terms, the present invention is an improved process for the thermal cracking of hydrocarbons which process comprises:

1. heating a hydrocarbon feedstock to a temperature of between about 1400° F and about 1900° F in a reaction zone containing a forced circulation riser and in the presence of a molten metal;
2. separating the resulting gaseous reaction products from the molten metal by gravity separation;
3. circulating the molten metal to a reheat zone and then back to the reaction zone;
4. routing the gaseous reaction products from the reaction zone through a transition zone to a quench zone containing a forced circulation riser, wherein the residence time of the gaseous reaction products in the transition zone is less than 0.02 seconds;
5. cooling the gaseous reaction products to a temperature of between about 800° F and about 1200° F in the quench zone by contacting the gaseous reaction products with the molten metal;
6. separating the resulting gaseous reaction products from the molten metal by gravity separation; and
7. circulating the molten metal to a heat removal zone and then back to the quench zone.

Also disclosed is an apparatus for the high temperature thermal cracking of a liquid or gaseous hydrocarbon in the presence of a molten metal which comprises:

1. a reaction zone having
   a. a vertical tubular reaction chamber which has an inlet for supplying a hydrocarbon feedstock, an inlet for supplying molten metal, and a reaction product outlet communicating with a hot product separation chamber,
   b. a hot product separation chamber communicating with the outlet of said reaction chamber having an outlet for separated reaction product and a liquid seal of molten metal communicating with a reheat chamber, and
   c. a reheat chamber which surrounds at least a major proportion of the reaction chamber, which reheat chamber has inlet and outlet means for passing molten metal from the hot product separation chamber to the reaction chamber and heating means for maintaining the temperature of the molten metal in the reaction zone at above 1400° F;

2. a transition zone communicating with the outlet of the hot product separation chamber of the reaction zone and communicating with the inlet of the cooling chamber of the quench zone; and
3. a quench zone having
   a. a vertical tubular cooling chamber communicating with the transition zone which has an inlet for the reaction product from the transition zone, an inlet for supplying molten metal, and a cooling chamber product outlet communicating with a cooled product separation chamber,
   b. a cooled product separation chamber communicating with the outlet of said cooling chamber having an outlet for separated cooled reaction product and a liquid seal of molten metal communicating with a heat removal chamber, and
   c. a heat removal chamber which surrounds at least a major proportion of the cooling chamber, which heat removal chamber has inlet and outlet means for passing molten metal from the cooled product separation chamber to the cooling chamber and cooling means for maintaining the temperature of the molten metal in the quench zone at between about 800° F and about 1200° F.

THE DRAWING

The drawing attached is a FIGURE which represents, in a diagrammatical cross-section, an example of an apparatus according to the present invention. Arrows are employed in the drawing to signify the direction of flow of the fluids.

Referring to the drawing, the reaction zone comprises a vertical tubular reaction chamber (a forced circulation riser) 1 disposed entirely within the reactor vessel 2. The reaction chamber 1 has inlet openings 3 for the molten metal. In the discharge side, the reaction chamber 1 communicates directly with the hot product separation chamber 4 through an opening 5. The separation chamber contains an inverted basin 6 which acts as a gas-liquid separator. The gaseous reaction products are separated from the molten metal and are routed through the transition zone 7 to the quench zone. The molten metal thus separated by the inverted basin separation plate falls to the liquid seal 8 and is circulated back to the reaction chamber through the openings 3. A reservoir of hot molten metal (reheat zone) surrounds the reaction chamber. A heating system 9 is employed to maintain the temperature in the reaction chamber at between 1400° F and 1900° F. A feed line 10 for the gaseous or liquid hydrocarbon feed communicates with a nozzle 11 axially situated in the reaction chamber 1 in the immediate vicinity of the openings 3. If desired, multiple nozzles may be employed for better distribution of the hydrocarbon feed in the riser. Preferably, steam 12 is added to the reaction chamber to reduce the partial pressure of the hydrocarbon and assist in the circulation of the feed-molten metal dispersion within the reaction chamber. If desired, the steam 12 may be combined with the hydrocarbon feed through valve 13 thereby also promoting the atomization of the feed by the nozzle 11. In addition, the steam 12 may be added to the reaction chamber separately from the feed through valve 14 and nozzle 15 located within the riser and below the hydrocarbon feed nozzle 11. By injecting steam within the riser and below the feed nozzle, it is possible to prevent the buildup of a coke necklace on the walls of the riser near the feed nozzle. Preferably, about 10 to 25% of the total steam added to the system is injected through nozzles located as is nozzle 15. Multiple steam nozzles and steam injection locations may be employed within the reaction chamber so as to improve the fluid dynamics.

If necessary, an optional skimming device may be employed to remove accumulated coke and sludge from the surface of the molten metal reservoir (the liquid seal 8) in the hot product separation chamber 4.

The level of the molten metal in the reservoir in the hot product separation chamber 4 is adjusted to maintain a minimum distance between the level 8 and the separation plate 6 consistent with operational dynamics so as to keep to a minimum the volume, and hence residence time, of the gaseous reaction products as they pass from the reaction zone through the transition zone and to the quench zone. Accordingly, the size of the transition zone 7 is designed so that the residence time of the gaseous products in the transition zone is less than about 0.02 seconds.

The gaseous products exit the transition zone 7 and enter the cooling chamber 16 through opening 17. Optionally, an inverted basin or dollar plate 18 is employed to distribute the gaseous products within the cooling chamber 16. The cooling chamber 16 is a forced circulation riser and is disposed entirely within the cooling vessel 19. The cooling chamber 16 has inlet openings 20 for the molten metal, which communicate directly with the cooled product separation chamber 21. On the discharge side, the cooling chamber 16 communicates directly with the cooled product separation chamber 21 through an opening 22. The cooled product separation chamber 21 contains an inverted basin 23 which acts as a liquid-gas separator. The gaseous reaction products exit the quench zone along opening 24. The molten metal thus separated falls onto the surface 25 of the molten metal reservoir (heat removal zone) in the cooling vessel 19 and is then circulated back to the cooling chamber 16. A cooling system 26, such as steam generating coils, is employed to maintain the temperature in the quench zone at between about 800° F and about 1200° F.

Significantly, the gaseous reaction products entering the quench zone from the reaction zone contain entrained molten metal. In a preferred embodiment, a weir 27 is employed to maintain the liquid level 25 in the cooled product separation chamber. Accordingly, the entrained molten metal increases the quantity of molten metal in the quench zone, then overflows the weir and is returned to the reaction zone along conduit 28.

The residence time in the cooled product separation chamber 21 is not critical so that a secondary separation or a high efficiency primary separation can be used to eliminate any lead carryover from the quench zone.

The above embodiment is described for purposes of illustration only and should not be construed as a limitation on the claims.

DETAILED DESCRIPTION OF THE INVENTION

The present invention is particularly suited to the cracking of gaseous and liquid hydrocarbons such as refinery gas, gasoline range material, naphthas, and gas oils. Further, it is possible to crack heavy hydrocarbons such as residual oils and crude oils according to the invention.

The gaseous reaction products produced according to the invention are primarily lower olefins such as ethylene and propylene. When employing the process according to the present invention to produce a given ethylene production rate, methane and ethane production are reduced as is the required feed rate resulting in savings in downstream recovery sections (process gas and refrigeration compression horse power).

The metals employed in the invention must be molten at processing temperatures, must have a melt point below 1000° F, and have a high specific heat. Useful metals include lead, tin, zinc, bismuth and cadmium or alloys of these elements in a molten state. A preferred metal is a lead-bismuth alloy since it has a lower melting point thus allowing start-up melting to be done with steam and preventing possible solidification around the cooling coils in the quench zone. Also, the lead-bismuth alloy is less corrosive than lead alone. A useful lead-bismuth alloy is 60 percent lead and 40 percent bismuth.

The operating conditions in the reaction chamber vary depending primarily upon the type of hydrocarbon feed employed. Reaction chamber temperature typically varies from about 1400° F to about 1900° F. When cracking gas oil, reaction temperatures are typically about 1580° F to about 1650° F whereas when cracking ethane the temperatures typically range from about 1700° F to about 1800° F. Reaction zone pressure varies typically from atmospheric pressure to about 50 psig, preferably about 15 psig to about 25 psig. The average residence time of the hydrocarbon feed in the reaction chamber has a significant effect on the yield characteristics of the product and typically varies from about 0.02 seconds to about 0.5 seconds, preferably about 0.05 seconds to about 0.1 seconds.

Because of the short residence time in the reaction chamber, it is necessary that the molten metal and feed be mixed very rapidly. Accordingly, a preferred method of admixing is to entrain the molten metal into a high velocity stream of feed by such means as an ejector in which the feed is the entrained fluid. Due to this intimate mixing of the molten metal and feed, one of the fluids is in a state of very fine dispersion in the other.

There must be some means employed to keep the metal molten in the reaction zone. One suitable means is indirect heat exchange with a tube bank located in the reheat zone of the reactor vessel. Flowing through the tubes may be a heat exchange material such as hot combustion gases from a furnace.

It is preferred that steam be added to the reaction chamber. In addition to aiding in the circulation, the steam lowers the partial pressure of the hydrocarbon feed thereby improving conversion and yield structure and reducing coking tendency. The weight ratio of steam to hydrocarbon feed typically varies from about 0.5:1 to about 1:1, preferably about 0.6:1 to about 0.8:1.

The gaseous reaction products are separated from the molten metal in the reaction zone and pass through the transition zone to the quench zone. Until the products are quenched in the quench zone, the olefins present tend to polymerize and form coke. In order to minimize the formation of coke, the transition zone should be sized so that the reaction products flowing through the transition zone have an average residence time of less than about 0.02 seconds. An important consideration in minimizing the average residence time in the transition zone is the level of the molten metal in the separation zone (the liquid seal). The liquid seal should be adjusted to maintain a minimum distance between the liquid seal and the separation plate consistent with operation dynamics.

The separation plate positioned over the reaction chamber in the reaction zone and over the cooling chamber in the quench zone is preferably shaped like an inverted basin. A dollar plate may be employed, but is not as effective in separating the gas product from the molten metal as is an inverted pot separator.

An important characteristic of the present invention is that the separation efficiency within the reaction zone prior to quench need not be as high as in other systems not employing the same molten media for reaction heat transfer media and for quench media. In the present invention, any molten metal entrained with the reaction products from the reaction zone will be recovered in the quench zone where the molten metal can then be recycled to the reaction zone.

The residence time of the gaseous products in the quench zone is not critical. Accordingly, the gas-liquid separator in the quench zone can be designed to achieve nearly 100% efficiency therein preventing any appreciable loss of molten metal from the system. The average residence time of the gaseous reaction products in the cooling chamber and cooled product separation chamber is typically about 0.1 seconds to about 1.0 seconds. Quench zone temperatures range from about 800° F to 1200° F, preferably, about 900° F to about 1100° F. Quench zone pressures correspond roughly with reaction zone pressures.

An essential characteristic of the present invention is the use of forced circulation risers in both the reaction zone and the quench zone. The circulation through the risers is accomplished through a combination of the jet action of and gas lift from the high velocity of the hydrocarbon feed through the feed nozzles and the action of the steam introduced either through the hydrocarbon feed nozzle or a separate steam nozzle located in the riser below the hydrocarbon feed nozzle. These forced circulation risers, contrary to the operation of reactors employing dip tubes, result in fairly stable operation and little entrainment.

What is claimed is:

1. In a process for the thermal cracking of hydrocarbons in which a liquid or gaseous hydrocarbon feedstock selected from the group consisting of refinery gas, gasoline range material, naphthas, gas oils, residual oils, crude oils and mixtures thereof is introduced into a bath of molten metal in a reaction zone and in which gaseous reaction products comprising primarily ethylene and propylene are separated from the molten metal which is circulated back to the reaction zone, the improvement which comprises:
   a. heating said hydrocarbon feedstock to a temperature of between about 1400° F and 1900° F in a reaction zone containing a forced circulation riser and in the presence of a molten metal wherein said feedstock is injected into said forced circulation riser thereby providing circulation of the hydrocarbon feedstock/ molten metal mixture within the reaction zone;
   b. separating the resulting gaseous reaction products from the molten metal by gravity separation;
   c. circulating the molten metal to a reheat zone surrounding the forced circulation riser and then back to the reaction zone;
   d. routing the gaseous reaction products from said reaction zone through a transition zone to a quench zone containing a forced circulation riser, wherein the residence time of said gaseous reaction products in said transition zone is less than 0.2 seconds;

e. cooling said gaseous reaction products to a temperature of between about 800° F and about 1200° F in said quench zone by contacting said gaseous reaction products with a cooler molten metal;

f. separating the resulting gaseous reaction products from said cooler molten metal by gravity separation; and g. circulating the cooler molten metal to a heat removal zone and then back to said quench zone.

2. The process according to claim 1 wherein the average residence time of the feed and reaction products with the molten metal in said reaction zone is less than 0.1 seconds.

3. The process according to claim 1 wherein steam is introduced into the reaction zone along said hydrocarbon feedstock.

4. The process according to claim 3 wherein the weight ratio of steam to hydrocarbon feed is between about 0.5:1 and about 1:1.

5. The process according to claim 1 wherein any molten metal entrained with said gaseous reaction products from said reaction zone to said quench zone is recycled from said quench zone to said reaction zone.

6. The process according to claim 1 wherein said molten metal is lead.

7. The process according to claim 1 wherein said molten metal is a lead-bismuth alloy.

* * * * *